Figure 1:
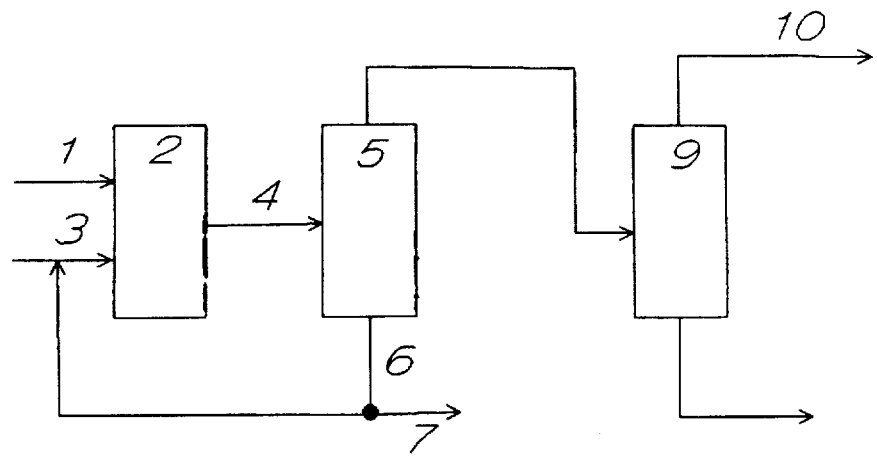

United States Patent [19]
Arnoldy et al.

[11] Patent Number: 5,756,828
[45] Date of Patent: May 26, 1998

[54] CARBONYLATION REACTIONS

[75] Inventors: Peter Arnoldy; Patricia Johanna Anna Marie Giltay; Johannes Jacobus Keusper, all of Amsterdam; Theodoor Johan Leonard Wenceslaus Simons, The Hague, all of Netherlands

[73] Assignee: Shell Oil Company, Houston, Tex.

[21] Appl. No.: 742,286

[22] Filed: Nov. 4, 1996

[30] Foreign Application Priority Data

Mar. 11, 1995 [EP] European Pat. Off. ............ 95202986

[51] Int. Cl.$^6$ .................... C07C 67/36; C07C 51/14
[52] U.S. Cl. ................................ 560/207; 562/522
[58] Field of Search ......................... 560/207; 562/522

[56] References Cited

U.S. PATENT DOCUMENTS

| | | | |
|---|---|---|---|
| 4,013,583 | 3/1977 | Knifton | 562/522 |
| 4,013,584 | 3/1977 | Knifton | 562/522 |
| 4,257,973 | 3/1981 | Mrowca | 562/522 |
| 4,733,006 | 3/1988 | Singleton et al. | 562/519 |
| 4,739,109 | 4/1988 | Drent | 560/207 |
| 4,739,110 | 4/1988 | Drent | 560/207 |
| 4,767,574 | 8/1988 | Hanes et al. | 560/207 |
| 4,861,912 | 8/1989 | Drent et al. | 560/204 |
| 4,940,787 | 7/1990 | Drent et al. | 560/207 |
| 5,177,253 | 1/1993 | Drent et al. | 560/207 |
| 5,258,546 | 11/1993 | Klusener | 560/207 |

*Primary Examiner*—Paul J. Killos

[57] ABSTRACT

The invention provides a process for the carbonylation of an olefinically or acetylenically unsaturated compound which comprises:
(a) reacting the unsaturated compound with carbon monoxide and a co-reactant in the presence of a carbonylation catalyst, obtainable by combining a source of platinum group metal cations, a phosphine ligand and an anion, to produce a reaction mixture comprising a carbonylation product, the carbonylation catalyst, and excess of the olefinically or acetylenically unsaturated compound and/or the co-reactant, and
(b) recovering the carbonylation product by distillation of the reaction mixture wherein a catalytically active concentrate is removed from the reaction mixture prior to step (b).

15 Claims, 1 Drawing Sheet

CARBONYLATION REACTIONS

The invention relates to carbonylation reactions. More in particular, the invention relates to a process for the carbonylation of an olefinically or acetylenically unsaturated compound, which comprises reacting the unsaturated compound with carbon monoxide and a co-reactant in the presence of a carbonylation catalyst, obtainable by combining a source of platinum group metal cations, a phosphine ligand and an anion.

As is known from SRI International PEP Report 11D, Shell has developed a route for preparing amongst others methyl methacrylate (MMA) from propyne using a homogeneous palladium-phosphine carbonylation catalyst. Although this route is already more attractive from an economic point of view than the competing routes discussed in this Report, there is still the incentive to further lower the cost, in particular the cost related to the relatively expensive carbonylation catalyst. It would hence be desirable to lower the catalyst cost. This could either be effected through use of even lower concentrations of catalyst, or through catalyst recovery and recycle.

It is known (page 9–13 of the Report) that homogeneous catalysts, especially those with ligands, are susceptible to slow deactivation and poisoning due to accumulation of impurities. Decreasing the content of the carbonylation catalyst in the reaction mixture and increasing the residence time, therefore, is not only cumbersome because of the already very low concentrations, but also suffers from increased sensitivity to poisons. Moreover, at longer residence times the catalyst may suffer from deactivation as the result of ligand degradation.

According to the Report and the literature cited therein, the activity of a recirculating carbonylation catalyst, collected as bottom stream of the MMA distillation column, is believed to be maintained by withdrawing a small purge to control the build-up of impurities (cf. page E-25 of the Report). The purge stream is then to be treated as discussed below, to separate the valuable components for reuse. Alternatively, the purge could be packaged and shipped to the palladium supplier or to a custom processor.

As set out in the Report, the purge stream may be treated similar to purge streams containing rhodium/triphenylphosphine catalysts. Purge streams containing rhodium/triphenylphosphine catalysts are concentrated under vacuum in a wiped-film evaporator (WFE) to remove some of the ligand and light impurities. Batches of the condensed stream are extracted to leave a residue that is mostly ligand for reuse. Rhodium metal residue from the WFE is treated with air to oxidise the remaining ligand, then washed with acid and solvent. The rhodium is converted to the active species and mixed with fresh and recovered ligand.

Although the process as envisaged by the authors of the Report may be operable, one has to realise that this bottom stream has a significantly reduced catalytic activity and hence needs to be treated almost in full. Naturally this elaborate treatment is preferably avoided.

In EP-A-0,571,044 (cf. page 4, lines 33–36) a process for the recovery of a carboxylate ester reaction product is described which may involve a step of separating a stream comprising heavy ends having a volatility lower than the volatilities of the reaction product and the azeotrope-forming alcohol precursor. This tailing of heavy ends can be effected using common chemical technology, for example distillation. The product of such distillation step, however, has again significantly reduced catalytic activity.

Surprisingly, the inventors have found that when a carbonylation catalyst, obtainable by combining a source of platinum group metal cations, a phosphine ligand and an anion is concentrated before distillation of the carbonylation product, the concentrate may still retain sufficient activity to be reused as carbonylation catalyst without the proposed oxidative treatment step.

Accordingly, the invention provides a process for the carbonylation of an olefinically or acetylenically unsaturated compound which comprises:

(a) reacting the unsaturated compound with carbon monoxide and a co-reactant in the presence of a carbonylation catalyst, obtainable by combining a source of platinum group metal cations, a phosphine ligand and an anion, to produce a reaction mixture comprising a carbonylation product, the carbonylation catalyst, and excess of the olefinically or acetylenically unsaturated compound and/or the co-reactant, and (b) recovering the carbonylation product by distillation of the reaction mixture wherein a catalytically active concentrate is removed from the reaction mixture prior to step (b).

Preferably, the catalytically active concentrate is removed by separating-out the remaining components of the reaction mixture at ambient or elevated temperature up to about 150° C., preferably no more than 100° C., and normal or subatmospheric pressure, provided that the residence time at elevated temperatures is less than 20 minutes.

In a preferred embodiment, the catalytically active concentrate is removed by concentration in an evaporator, whereby an at least a three-fold concentration of the carbonylation catalyst is achieved within a residence time of the reaction mixture that is less than 20 minutes.

Typically, the evaporator is a film evaporator such as described in Perry's Chemical Engineer's Handbook (6th ed., 11.31–11.38). Film evaporators that may be applied very successfully are falling film evaporators and wiped film evaporators. The evaporator may be a single evaporator, or a train of evaporators, operating in parallel or serial. Preferably, the carbonylation catalyst is concentrated at least three-fold, more preferably at least six-fold, within a time span of 20 minutes.

The reactants of the process, i.e., the olefinically or acetylenically unsaturated compound as well as the co-reactant may be any of those mentioned in EP-A-0,495, 547.

The unsaturated compound may be an olefinically unsaturated compound up to 30 carbon atoms including compounds having a plurality of unsaturated carbon-carbon bonds and/or compounds having one or more functional groups, or an acetylenically unsaturated compound up to 30 carbon atoms including compounds having a plurality of unsaturated carbon-carbon bonds and/or compounds having one or more functional groups. Preferably, the unsaturated compound is an acetylene, suitably ethyne or propyne.

Suitable co-reactants in case of the olefin include molecular hydrogen to prepare oxo-aldehydes and oxo-alcohols and nucleophilic compounds, such as lower alcohols having 1 to 6 carbon atoms, having one or more active hydrogen atoms. An example of the latter includes butanol, to prepare solvents like butylproprionate. Suitable co-reactants in case of the acetylene include water or a lower alcohol such as methanol (MeOH) to prepare for instance acrylic acid, methacrylic acid, methyl acrylate or methyl methacrylate (MMA). The invention is particularly useful in the production of MMA.

The reactants are preferably fed to the process in substantial accordance with the reaction stoichiometry, i.e., in substantially equimolar amounts apart from any recycle streams, although the ratio in the carbonylation section may differ from stoichiometry to expedite the reaction. For instance, the ratio in the carbonylation section of propyne/ carbon monoxide/methanol, to produce MMA, is in the range of 1:1–4:1–4, typically in the range of a:1–2:1–2, preferably about 1:1.5:1.5–1.9.

In the present specification the metals of the platinum group are defined as the metals with the atomic numbers 28, 46 and 78, i.e. nickel, palladium and platinum. Of these, palladium and platinum are preferred. Best results have been achieved with carbonylation catalysts based on palladium cations and they are therefore most preferred.

Examples of suitable metal sources are nickel, platinum or palladium compounds such as salts of nickel, platinum or palladium and nitric acid, sulphuric acid, sulphonic acids or carboxylic acids with up to 12 carbon atoms, nickel-, palladium- or platinum complexes, e.g. with carbon monoxide or acetylacetonate, or the metal combined with a solid material such as an ion exchanger or carbon. Palladium(II) acetate and platinum(II) acetylacetonate are examples of preferred metal sources.

As anion source, any compound generating anions may be used. Suitably, acids, or salts thereof, are used as source of anions, for example any of the acids mentioned above, which may also participate in the salts of the metals of the platinum group.

In the carbonylation catalysts of the invention, preferably strong acids are used as anion source, i.e. acids having a pKa value of less than 3, preferably less than 2, measured in aqueous solution at 18° C. The anions derived from these acids are non-coordinating or weakly coordinating with the metals of the platinum group.

Typical examples of suitable anions are anions of phosphoric acid, sulphuric acid, sulphonic acids and halogenated carboxylic acids such as trifluoroacetic acid.

Sulphonic acids are in particular preferred, for example methanesulphonic acid, trifluoromethanesulphonic acid, tert-butanesulphonic acid, p-toluenesulphonic acid and 2,4, 6-trimethylbenzenesulphonic acid.

Also, complex anions are suitable, such as the anions generated by a combination of a Lewis acid such as $BF_3$, $AlCl_3$, $Sn(CF_3SO_3)_2$, $SnF_2$, $SnCl_2$, $GeCl_2$ or $PF_5$, with a protic acid, such as a sulphonic acid, e.g. $CF_3SO_3H$ or $CH_3SO_3H$ or a hydrohalogenic acid such as HF of HCl, or a combination of a Lewis acid with an alcohol. Examples of suitable complex anions are $BF_4^-$, $[SnCl_2.CF_3SO_3]^-$, $SnCl_3^-$ and $PF_6^-$.

As ligand both monodentate phosphines and bidentate diphosphines may be used. Specific examples include triphenylphosphine, diphenyl(2-pyridyl)phosphine, 1,2-P,P'-bis(9-phosphabicyclo[3.3.1 or 4.2.1]nonyl)ethane, etc. In the carbonylation of acetylenes preferably diphenyl(2-pyridyl)phosphine is used.

Carbonylation catalysts suitably used are disclosed, for instance, in EP-A-0,271,144; EP-A-0,271,145; EP-A-0,274, 795; EP-A-386,833; EP-A-0,386,834; EP-A-0,495,547; WO 94/21585; WO 95/05357 and EP-A-0,499,329.

The most preferred carbonylation catalyst in the carbonylation of acetylenes is thus formed by combining (a) palladium(II) acetate, (b) diphenyl(2-pyridyl)phosphine, and (c) methanesulphonic acid.

The carbonylation catalyst may contain further components such as polymerisation inhibitors and the like. Suitably, a polymerisation inhibitor such as hydroquinone is included.

The quantity in which the carbonylation catalyst is used, is not critical and may vary within wide limits. Usually amounts in the range of $10^{-8}$ to $10^{-1}$, preferably in the range of $10^{-7}$ to $10^{-2}$ mole atom of platinum group metal per mole of unsaturated compound are used. The amounts of the participants in the carbonylation catalyst are conveniently selected such that per mole atom of platinum group metal from 0.5 to 100, preferably from 1 to 50 moles of ligand are used, from 0.5 to 100, preferably from 1 to 50 moles of anion source or a complex anion source.

The carbon monoxide reacted in the carbonylation step of the present process, can be derived from any source. It is preferably used in substantially pure form.

The carbonylation can be suitably carried out at moderate reaction conditions. Hence temperatures in the range of 20° to 200° C. are recommended, preferred temperatures being in the range of 30° to 120° C. Reaction pressures in the range of 5 to 100 bar absolute are preferred, lower or higher pressures may be selected, but are not considered particularly advantageous. Moreover, higher pressures require special equipment provisions.

Preferably, the process is carried out in a continuous manner, e.g., as described in EP-A-0,521,578.

The invention will be further illustrated by the drawings. Herein, FIG. 1 shows a flow scheme of a preferred embodiment of the invention. In this figure, the olefinically or acetylenically unsaturated compound is fed through line 1, to a carbonylation unit 2, which may be constituted by a plurality of individual reactors. In this unit 2 further reactants such as carbon monoxide, alcohol and catalyst are introduced either jointly with the unsaturated compound through line 1 or separately through a single or multitude of lines 3 (only one line shown). The reaction mixture is forwarded through line 4 to evaporator 5, e.g., an FFE. The evaporated reaction mixture is forwarded to a distillation zone 9, which again may be constituted of a plurality of distillation units. The carbonylation product is mainly collected as overhead stream 10, whereas the bottom stream 11 contains among others methyl crotonate. A catalytically active concentrate is collected from the evaporator 5 through line 6. Part thereof is purged through line 7. Together with ligand and/or anion to make-up for losses, if any, the remainder of the concentrate is recycled to unit 2.

Figure 2:
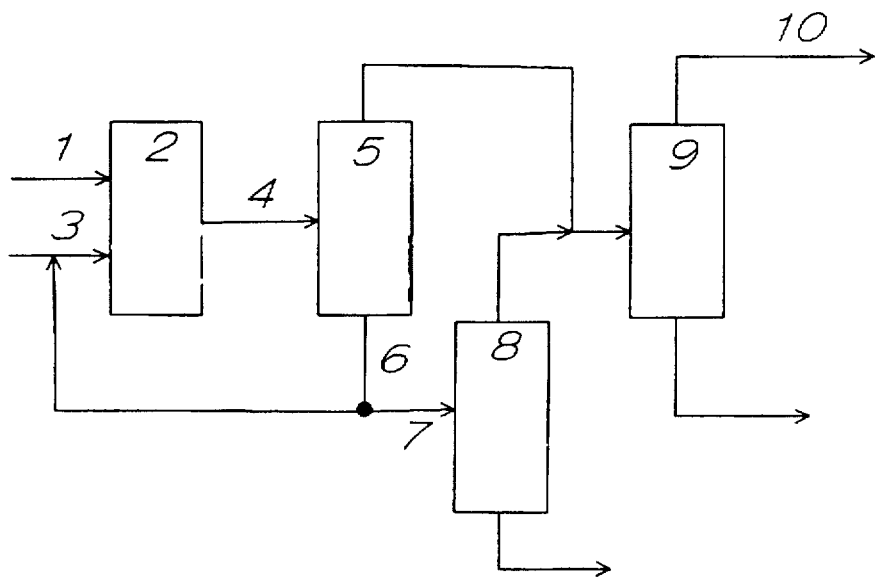

In FIG. 2, part of a more preferred embodiment is shown, similar to FIG. 1, but wherein the purge is passed through line 7 to a subsequent evaporator 8, for instance a WFE, to provide an evaporated stream that is combined with the evaporated reaction mixture, and a concentrated purge.

The design and operation of the carbonylation unit and further work-up equipment are within the skills of a chemical technologist, and does not require further explanation.

The invention will be illustrated by the non-limiting examples, as described hereinafter.

EXAMPLES

A fresh carbonylation feed consisting of a mixture of 32 mL/h propyne, 46 mL/h catalyst solution, and 15 NL/h CO was continuously fed to a continuously stirred tank reactor operating at a constant temperature of 45° C. A liquid level of 220 mL was maintained and the pressure was kept at 11 bar abs by means of a constant pressure valve. The catalyst solution contained MeOH, palladium-acetate ($Pd(OAc)_2$), diphenyl(2-pyridyl)phosphine (PN), methanesulphonic acid (MSA), and hydroquinone (HQ). The catalyst molar ratio Pd/PN/MSA was 1/20/20, the molar HQ/Pd ratio was 40 and the Pd-concentration amounted to 18 ppmw. The reaction mixture, i.e., the liquid reactor effluent containing MMA, unreacted feedstocks, and the catalyst components, was collected. After 16 h the steady-state conversion of propyne was found to be 89% mol, whereas the selectivity to MMA was found to be 99.2% mol. Next, the feed flows were increased to 77 mL/h catalyst solution, 64 mL/h propyne, and 30 NL/h CO. Again the liquid reactor effluent was collected. After 5 h a steady-state conversion of 83% mol was measured with a selectivity to MMA of 99.2% mol.

In total, 1827 g of liquid reactor effluent (containing 9.5 ppmw Pd) was thus collected and submitted to a WFE, applying a wall temperature of 85° C. and a pressure of 800 mbar abs. Two product streams were obtained; the evaporated product, consisting mainly of MeOH and MMA, and a bottom fraction, weighing 285 g and containing the catalyst components (60.9 ppmw Pd). The concentration factor in this example was 6.4, at a calculated residence time on the 'hot wall' of the WFE of less than 6 minutes.

To this fraction 625 g of MeOH was added together with 0.45 g of PN, 0.08 g of MSA, and 0.68 g of HQ. No Pd-component was added. The thus obtained mixture, which contained 18 ppmw of Pd as above, was used as a catalyst solution in a following carbonylation run.

Thus, to the CSTR 28 mL/h of this solution was fed together with 22 mL/h propyne and 10 NL/h CO applying similar conditions as set out above. After 16 h the steady-state conversion of propyne was measured to be 78% mol with a selectivity of 98.8 mol %. Next, the feed flows were increased to 76 mL/h, 65 mL/h and 30 NL/h, respectively. After 5 h the steady-state conversion was measured to be 64% mol with a selectivity to MMA of 98.8% mol.

It can be seen that in the second run the Pd-catalyst still exhibits a significant activity.

COMPARATIVE EXAMPLES 15 mL of a bottom stream from a MMA distillation column as described in the SRI International PEP Report 11D, containing 124 ppmw Pd and other catalyst residues in 90% w MMA and 10% w methyl crotonate, was diluted with 30 mL of MeOH containing 0.7 mmol of PN, MSA, and HQ. The mixture was transferred to a 250 mL batch autoclave which was subsequently closed, filled with 60 bar abs of CO, and brought to 60° C. after which 175 mmol of propyne was added. After 5 h the reaction was completed as indicated by a leveling-off of the pressure drop. Turn-over in 5 h was 12,500 mol propyne per mol Pd or 2500 mol/mol/h.

The above procedure was followed but fresh MMA (p.a.) was used without any Pd-catalyst residues. In the MeOH 0.7 mmol of PN-ligand, MSA, and HQ were dissolved plus 0.014 mmol of $Pd(OAc)_2$. After less than 0.5 h the pressure drop has leveled-off and the turn-over was found to be more than 25,000 mol/mol/h.

The first example proofs that the bottom stream of the MMA distillation column has a significantly reduced activity, i.e., an activity which is only 10% of that of a fresh catalyst. On the other hand, in the example according to the invention about 50% of the activity has been retained.

We claim:

1. A process for the carbonylation of an olefinically or acetylenically unsaturated compound, the process comprising the steps of:
   (a) reacting the unsaturated compound with carbon monoxide and a co-reactant in the presence of a carbonylation catalyst, the carbonylation catalyst obtainable by combining a source of platinum group metal cations, a phosphine ligand and an anion, to produce a reaction mixture comprising a carbonylation product, the carbonylation catalyst, and excess of the unsaturated compound, the co-reactant, or both; and
   (b) recovering the carbonylation product by distillation of the mixture, wherein a catalytically active concentrate is removed from the reaction mixture prior to step (b).

2. The process of claim 1 wherein the reaction mixture is concentrated in an evaporator, whereby an at least three-fold concentration of the carbonylation catalyst is achieved within 20 minutes.

3. The process of claim 1 wherein the unsaturated compound is an acetylenically unsaturated compound.

4. The process of claim 1 wherein the unsaturated compound is ethyne.

5. The process of claim 1 wherein the unsaturated compound is propyne.

6. The process of claim 1 wherein the co-reactant is a $C_{1-6}$ alcohol.

7. The process of claim 6 wherein the co-reactant is methanol.

8. The process of claim 1 wherein the co-reactant is water.

9. The process of claim 1 wherein the co-reactant is selected from the group consisting of molecular hydrogen and a nucleophilic compound having one or more active hydrogen atoms.

10. The process of claim 1 wherein the platinum group metal is palladium.

11. The process of claim 1 wherein the phosphine ligand is a monodentate phosphine.

12. The process of claim 1 wherein the phosphine ligand is diphenyl(2-pyridyl) phosphine.

13. The process of claim 1 wherein the anion is a non-coordinating anion.

14. The process of claim 1 wherein the catalytically active concentrate is removed from the reaction mixture in a falling-film evaporator.

15. The process of claim 14 wherein the falling film evaporator is a wiped film evaporator comprising a plurality of evaporators operating in series.

* * * * *